United States Patent [19]
Ishii

[11] Patent Number: 5,879,285
[45] Date of Patent: Mar. 9, 1999

[54] ALIGNING MEANS ATTACHING A CABLE IN AN IMAGING APPARATUS

[75] Inventor: Hiroshi Ishii, Hachioji, Japan

[73] Assignee: Olympus Optical Co., Ltd., Tokyo, Japan

[21] Appl. No.: 657,548

[22] Filed: Jun. 4, 1996

[30] Foreign Application Priority Data

Sep. 28, 1995 [JP] Japan ..................................... 7-251500

[51] Int. Cl.$^6$ ....................................................... A61B 1/05
[52] U.S. Cl. ............................... 600/110; 600/130; 348/75
[58] Field of Search .................................... 600/109, 110, 600/112, 129, 130; 348/65, 75

[56] References Cited

U.S. PATENT DOCUMENTS

| | | | |
|---|---|---|---|
| 4,745,470 | 5/1988 | Yabe et al. | 600/130 |
| 4,809,680 | 3/1989 | Yabe . | |
| 4,993,405 | 2/1991 | Takamura et al. | 600/110 |
| 5,609,561 | 3/1997 | Uehara et al. | 600/112 |

FOREIGN PATENT DOCUMENTS 5-161602  6/1993  Japan .

*Primary Examiner*—John P. Leubecker
*Attorney, Agent, or Firm*—Armstrong, Westerman, Hattori, McLeland, & Naughton

[57] ABSTRACT

An imaging apparatus has a printed-circuit board electrically connected to a solid-state imaging device, and a composite cable electrically connected to said printed-circuit board and made by bundling up a plurality of cables including at least one of plain cables and coaxial cables. An aligner for aligning the plurality of cables contained in the composite cable in a desired form is attached to the distal part of the composite cable. The distal side of the composite cable with the aligner attached to the distal part thereof is opposed to a plane of the printed-circuit board having electrodes. The conductors of the cables of the composite cable and the electrodes on the printed-circuit board are mutually connected all at once directly or indirectly via conducting patterns exposed on the distal side of the aligner. The work of connecting the cables of the composite cable to the electrodes on the printed-circuit board becomes simpler, and a rigid section becomes shorter.

19 Claims, 11 Drawing Sheets

ALIGNING MEANS ATTACHING A CABLE IN AN IMAGING APPARATUS

BACKGROUND OF THE INVENTION

1. Field of the Invention

The present invention relates to an imaging apparatus that includes a solid-state imaging device and a printed-circuit board connected to the solid-state imaging device and that has the printed-circuit board electrically connected to a composite cable. More particularly, this invention is concerned with a structure of connecting the printed-circuit board to the cables of the composite cable.

2. Description of the Related Art

In recent years, endoscopes having an elongated insertion unit thereof inserted in a body cavity in order to observe an organ in the body cavity or having if necessary a treatment appliance inserted in a treatment appliance channel in order to conduct various curative procedures or treatments have been adopted widely.

The endoscopes adopted as mentioned above include an electronic endoscope (hereinafter abbreviated to an endoscope) in which: a solid-state imaging device such as a CCD is placed in the distal part of the insertion unit thereof; an optical image formed on the CCD via an objective optical system is photoelectrically transferred into an electric signal; the electric signal is transmitted to a signal processing unit over a signal cable and converted into a video signal; and the video signal is visualized in a monitor screen.

The CCD in the endoscope and the signal processing unit that is an external unit are linked generally by a composite cable made by bundling up a plurality of cables in order to supply driving power to the CCD, transmit a video signal, or transmit a clock. For the composite cable, a coaxial cable is used as a signal line as a countermeasure against noises, and a plain cable is used as a power line.

When the cables contained in a composite cable are connected to a CCD or a printed-circuit board such as a hybrid IC (hereinafter an HIC) or flexible printed-circuit board (FPC) which is electrically connected to the CCD, the plurality of cables are separated from one another and then connected to electrodes formed on the printed-circuit board.

However, when cables contained in a composite cable are coaxial cables, the work of removing the armors of the coaxial cables is needed so that the conductors and shields of the coaxial cables can be soldered to different places. The work of removing the armors of the coaxial cables and connecting the coaxial cables is laborious. Moreover, a certain length of connection is needed to connect the coaxial cables to a printed-circuit board. This becomes an obstruct in reducing the diameter and length of an imaging apparatus.

An imaging apparatus employed in an endoscope is located in the distal part of an insertion unit of the endoscope. When the imaging apparatus is made shorter, the length of a rigid section of the distal part of the endoscope can be reduced, and inserting efficiency can be improved. The reduction in diameter and length of the imaging apparatus has been demanded even in an effort to improve the efficiency in inserting an endoscope.

In order to shorten an imaging apparatus, Japanese Patent Laid-Open No. 5-161602 has disclosed a structure in which: a printed-circuit board having ground electrodes formed on one side thereof and signal electrodes formed on the other side thereof, and having through holes for linking the electrodes is placed vertically; cables are passed through the through holes; and signal conductors and shields of the cables are connected to the signal electrodes and ground electrodes on the printed-circuit board. Using the art disclosed in the unexamined publication, cables can be connected to a printed-circuit board using only the thickness of the printed-circuit board. Shortening an imaging apparatus can be achieved.

However, when the art disclosed in the Japanese Patent Laid-Open No. 5-161602 is used to connect a composite cable to a printed-circuit board, the work of separating the cables of the composite cable from one another and the work of passing the respective cables through a through hole of the printed-circuit board and connecting them to electrodes are still necessary. For reinforcing the respective cables connected to the printed-circuit board, these mutually-separated cables are fixed all at once using an adhesive or the like. As a result, a rigid area made from the adhesive is formed on the rear side of the printed-circuit board. This makes it difficult to greatly shorten an imaging apparatus.

OBJECTS AND SUMMARY OF THE INVENTION

An object of the present invention is to provide an imaging apparatus making it easy to achieve the work of connecting the cables contained in a composite cable to electrodes on a printed-circuit board and making it possible to reduce the length of a rigid section.

The present invention is an imaging apparatus having a printed-circuit board electrically connected to a solid-state imaging device and a composite cable electrically connected to electrodes on the printed-circuit board and made by bundling up a plurality of cables including at least one of plain cables and coaxial cables, wherein:

an aligning means for aligning a plurality of cables contained in the composite cable in a desired form is attached to the distal part of the composite cable; and the distal side of the composite cable with the aligning means attached to the distal part thereof is opposed to a plane part of the printed-circuit board having the electrodes, and the conductors of the cables of the composite cable and the electrodes on the printed-circuit board are mutually connected all at once directly or indirectly via conducting patterns exposed on the distal side of the aligning means.

The other features and advantages of the present invention will be fully apparent from the description below.

BRIEF DESCRIPTION OF THE DRAWINGS

FIGS. 1 to 6 relate to the first embodiment of the present invention;

FIG. 1 is an explanatory diagram showing an outline configuration of an endoscope;

FIG. 2 is a sectional view for explaining the structure of a distal part of an endoscope;

FIG. 3 is an explanatory diagram showing a composite cable and an aligning means;

FIG. 4A is an end view;

FIG. 4B is a side view;

FIG. 5 is an electrode arrangement diagram showing electrodes that coincide with conductors placed in the aligning means shown in FIG. 4A and that are formed on an HIC board;

FIG. 6 is a sectional view for explaining a connected state of the composite cable and HIC board;

FIG. 7 is an explanatory diagram showing the distal side of a composite cable fixed by means of an adhesive;

FIG. 8 is an explanatory diagram showing the distal part of the composite cable with the end thereof machined and an aligning means;

FIG. 9 is an explanatory diagram showing the composite cable with the aligning means attached to the distal part thereof;

FIG. 10 is a layout of electrodes on an HIC board;

FIG. 11 is a sectional view for explaining a connected state of the composite cable and HIC board;

FIG. 12 is an explanatory diagram showing the structure of a composite cable;

FIG. 13 is a diagram showing a state in which coaxial cables having outer insulators thereof removed are arranged in two rows and fixed by means of an adhesive;

FIG. 14 is an explanatory diagram showing the distal part of a composite cable which is formed to have a desired shape and an aligning means;

FIG. 15 is an explanatory diagram showing the composite cable with the aligning means attached to the distal part thereof;

FIG. 16 is a layout of electrodes on an HIC board to which the composite cable with the aligning means attached is connected;

FIG. 17 is a sectional view for explaining a connected state of the composite cable and HIC board;

FIG. 18 is a diagram showing a state in which coaxial cables having outer insulators thereof removed are arranged in a row and fixed by means of an adhesive;

FIG. 19 is a sectional view for explaining a connected state in a CCD unit in an endoscope; and FIG. 20 is a detailed diagram showing area A of FIG. 19.

DETAILED DESCRIPTION OF THE PREFERRED EMBODIMENTS

FIGS. 1 to 6 show the first embodiment of the present invention.

Figure 1:
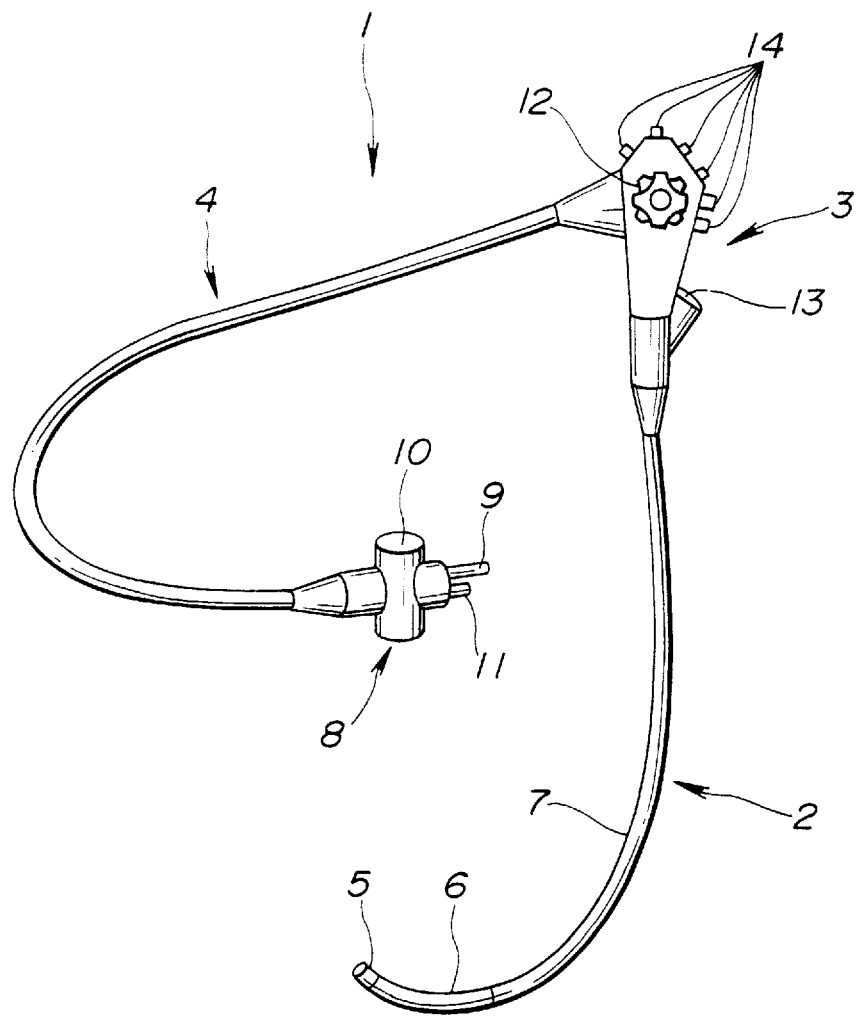

As shown in FIG. 1, an electronic endoscope (hereinafter an endoscope) 1 comprises an elongated insertion unit 2, an operation unit 3 located at the proximal end of the insertion unit 2 and gripped by an operator, and a flexible universal cord 4 that extends from the lateral side of the operation unit 3 and contains a light guide cable, signal cable, electrical cable, and the like.

The insertion unit 2 is made by orderly coupling a distal section 5 in which a solid-state imaging device such as a CCD is incorporated, a bending section 6 made by coupling a plurality of bending frames and capable of bending vertically and laterally, and a flexible tube 7 that is elongated and has flexibility.

A connector 8 is located at the proximal end of the universal cord 4. The connector 8 has a light guide connector 9 to be connected to a light source apparatus, an electrical contact 10 used to transmit an electric signal of an object image resulting from photoelectric transfer performed by a CCD, and an aeration base 11 used to supply air or the like to a nozzle in the distal section 5.

The operation unit 3 has an angulation knob 12 used to angle the bending section 6 vertically or laterally, a treatment appliance insertion port 13 used to insert a treatment appliance such as forceps to a body cavity, and a plurality of push-button switches 14 used to operate peripheral equipment such as a signal processing unit, a control unit, or an aeration, perfusion, and insufflation means.

Figure 2:
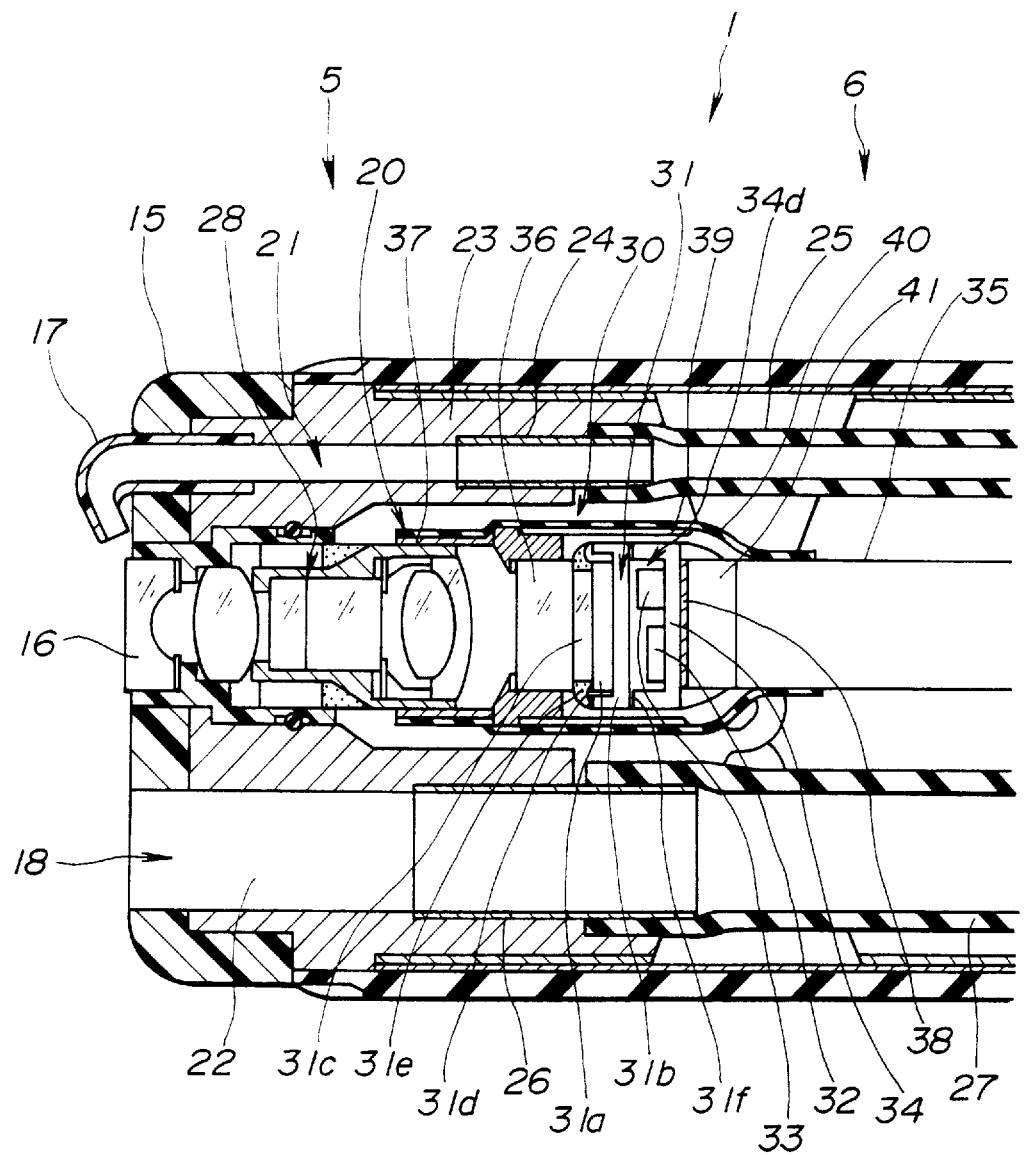

As shown in FIG. 2, a distal cover 15 constituting the distal section 5 located in the distal part of the insertion unit 2 of the endoscope 1 has an observation window 16, illumination lens (not shown), aeration/perfusion nozzle 17, and forceps opening 18. A distal block 23 including an imaging apparatus 20, aeration/perfusion bore 21, and forceps insertion bore 22, which communicate with the observation window 16, aeration/perfusion nozzle 17, and forceps opening 18 respectively, and constituting the distal section 5 is located behind the distal cover 15.

An aeration/perfusion pipe 24 is located at the back end of the aeration/perfusion bore 21 formed in the distal block 23. An aeration/perfusion tube 25 communicates with the aeration/perfusion pipe 24. A forceps insertion pipe 26 is located at the back end of the forceps insertion bore 22. A forceps insertion tube 27 communicates with the forceps insertion pipe 26.

The imaging apparatus 20 located in the distal block 23 comprises an objective optical unit 28 composed of a plurality of optical lenses, and a CCD unit 30 located behind the objective optical unit 28.

The CCD unit 30 consists mainly of a CCD 31 for receiving light incident to the objective optical unit 28, a hybrid IC board 34 (hereinafter an HIC board) on which an IC 32 for processing charges photoelectrically transferred by the CCD 31 into an electric signal and a chip capacitor 33 are mounted, and a composite cable 35 for transmitting an electric signal to a signal processing unit that is an external unit, for example, a composite cable containing a plurality of cables.

A cover glass 36 is affixed to a light receiving side of the CCD 31. The inner circumference of a CCD holding frame 37 is engaged with the outer circumference of the cover glass 36 and fixed unitedly thereto by means of an adhesive or the like.

The CCD 31 comprises a CCD chip 31a having an image pickup, ceramic package 31b, color filter 31c, bonding wire 31d, sealing resin 31e, electrodes 31f, and signal electrodes 31g.

The electrodes linked by the bonding wire 31d are electrically connected to the electrodes 31f via lines interconnected inside the ceramic package 31b.

The HIC board 34 has a concave part 34d in which the IC 32 and chip capacitor 33 are mounted. Similarly to the ceramic package 31b, an electrode is placed on both sides of the HIC board 34.

The electrode placed on the distal side of the HIC board 34 is connected to the electrode 31f of the CCD 31, while the electrode placed on a proximal-side plane of the HIC board 34 is connected to the distal side of the composite cable 35 via an anisotropic conducting sheet 38 as described later. A shield frame 39 is placed at the back end of the outer circumference of the CCD holding frame 37 in order to shield the CCD 31 and HIC board 34. The shield frame 39 and the distal part of the outer circumference of the CCD holding frame 37 are covered by a heat contraction tube 40.

Furthermore, the distal part of the composite cable 35 is covered by the back end of the heat contraction tube 40 and thus fastened thereby.

The CCD unit 30 ranges from the distal side of the CCD holding frame 37 to the back end of the composite cable 35. A rigid section of the imaging apparatus 20 ranges from the distal side of the objective optical unit 28 to the back end of the heat contraction tube 40. Reference numeral 41 denotes an insulating block serving as an aligning means that will be described later.

Now, the connection of the composite cable 35 and HIC board 34 will be described.

To begin with, the composite cable 35 will be described.

Figure 3:
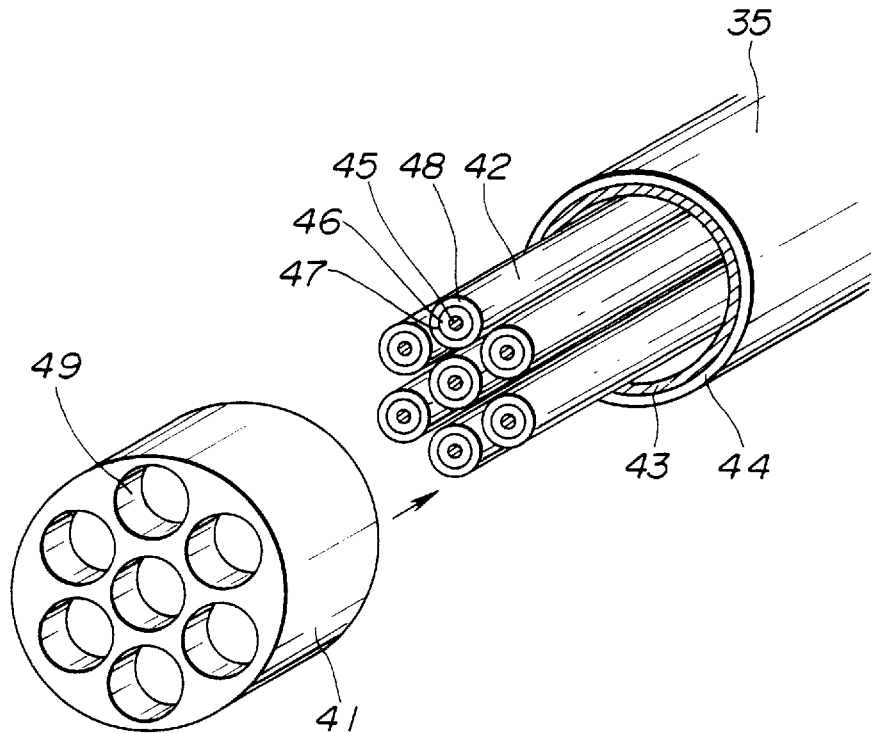

As shown in FIG. 3, the composite cable 35 connected to the electrode placed on the proximal-side plane of the HIC board 34 is a seven-core composite cable 35 made by bundling up seven coaxial cables 42. The outer circumference of the seven bundled coaxial cables 42 is covered by a synthetic shield 43. The synthetic shield 43 is coated with a synthetic coat 44.

Each of the coaxial cables 42 comprises an inner conductor 45 placed in the center thereof, an inner insulator 46 placed so that it encircles the inner conductor 45, an outer conductor 47 placed so that it encircles the inner insulator 46 and used to perform impedance matching for signal transmission, and an outer insulator 48 placed so that it encircles the outer conductor 47 and used as the outer circumference of the coaxial cable 42.

For forming the insulating block 41 serving as an aligning means as part of an united body, the distal part of the seven-core composite cable 35 has the synthetic coat 44 and synthetic shield 43 stripped off by the width of the insulating block 41, and has the seven coaxial cables 42 separated from one another.

The outer conductors 47, inner conductors 45, and synthetic shield 43 are made of an alloy of zinc plate and copper. Each inner conductor 45 is composed of seven stranded wires each having an outer diameter of 0.03 mm and has an outer diameter of 0.09 mm. Each outer conductor 47 is made by spirally winding a strand of 0.05 mm in diameter. The synthetic shield 43 is made by spirally winding a strand of 0.08 mm in diameter.

On the other hand, the outer insulators 48, inner insulators 46, and synthetic coat 44 are made of PFA. Each inner insulator 46 has a thickness of 0.05 mm and an outer diameter of 0.19 mm. Each outer insulator 48 has a thickness of 0.04 mm and an outer diameter of 0.37 mm. The synthetic coat 44 has a thickness of 0.1 mm and an outer diameter of 1.67 mm. These members and dimensions are not limited to the foregoing descriptions, but appropriate ones can be selected and set.

As illustrated, the insulating block 41 is formed with an insulating member made of a ceramic or the like. Seven cable locking holes 49 each having an inner diameter substantially agreeing with the outer diameter of each of the coaxial cables 42 are formed in a distal-side plane of the insulating block 41, so that they can retain the aligned state of the seven coaxial cables 42 contained in the seven-core composite cable 35.

The back side of the insulating block 41 serves as a cylindrical member having a concave part 41a (See FIG. 6), of which inner diameter substantially agrees with the inner diameter of the synthetic shield 43, formed. The outer diameter of the insulating block 41 is determined to substantially agree with the outer diameter of the seven-core composite cable 35.

For unitedly fixing the insulating block 41 to the distal part of the seven-core composite cable 35, first, the coaxial cables 42 that are separated from one another by stripping off the synthetic coat 44 and synthetic shield 43 are inserted in the opposed cable locking holes 49 one by one.

After the seven coaxial cables 42 are inserted in the cable locking holes 49, the insulating block 41 is pushed so that the back side of the insulating block 41 abuts on the stripped side of the seven-core composite cable 35, and thus secured.

At this time, since an adhesive is applied to the inner circumferential sides of the cable locking holes 49 and concave part 41a which are formed in the insulating block 41, to the outer circumferential sides of the coaxial cables 42, and to the stripped side of the seven-core composite cable 35, the insulating block 41 is unitedly fixed to the distal part of the seven-core composite cable 35 by means of the adhesive.

Figure 4A:
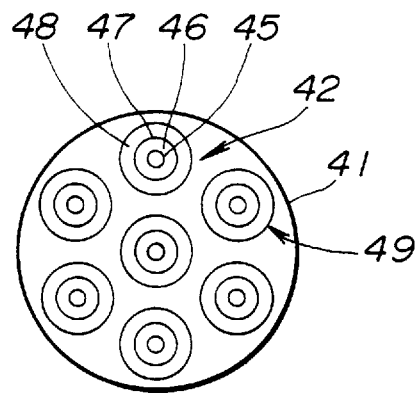
FIGS. 4A and 4B are explanatory diagrams showing the composite cable with the aligning means attached to the distal part thereof.
Figure 4B:
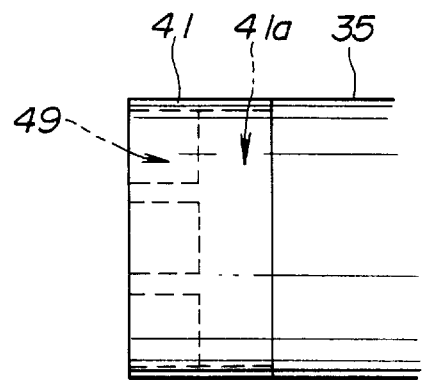

After the insulating block 41 is fixed to the distal part of the seven-core composite cable 35 by means of the adhesive, if the distal parts of the coaxial cables 42 are jutting out from the distal side of the insulating block 41, the jutting distal parts are cut out. Moreover, as shown in FIGS. 4A and 4B, polishing is carried out so that the distal sides of the coaxial cables 42 become coincident with the distal side of the insulating block 41. Thus, the seven-core composite cable 35 having the insulating block 41 unitedly attached to the distal part thereof is materialized.

Next, the HIC board 34 will be described.

Figure 5:
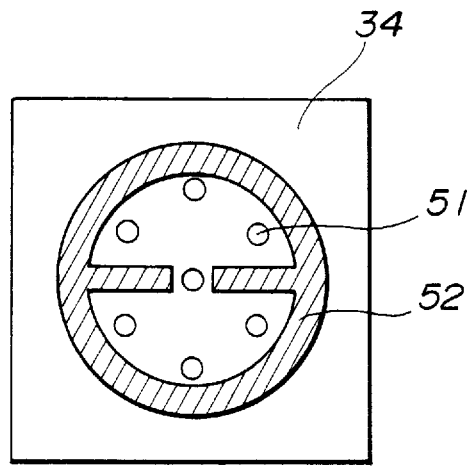

As shown in FIG. 5, on the proximal-side plane of the HIC board 34 to which the conductors arranged on the distal side of the insulating block 41 unitedly attached to the distal side of the seven-core composite cable 35, signal electrodes 51 coincident with the inner conductors 45 of the seven coaxial cables 42 of the seven-core composite cable 35, and ground electrodes 52 coming into contact with the outer conductors 47 of the seven coaxial cables 42 of the seven-core composite cable 35 all at once are jutting out. The ground electrodes 52 are formed to surround the signal electrodes 51.

The connection of the seven-core composite cable 35 having the insulating block 41 attached to the distal part thereof which is structured as mentioned above and the HIC board 34 will be described.

Figure 6:
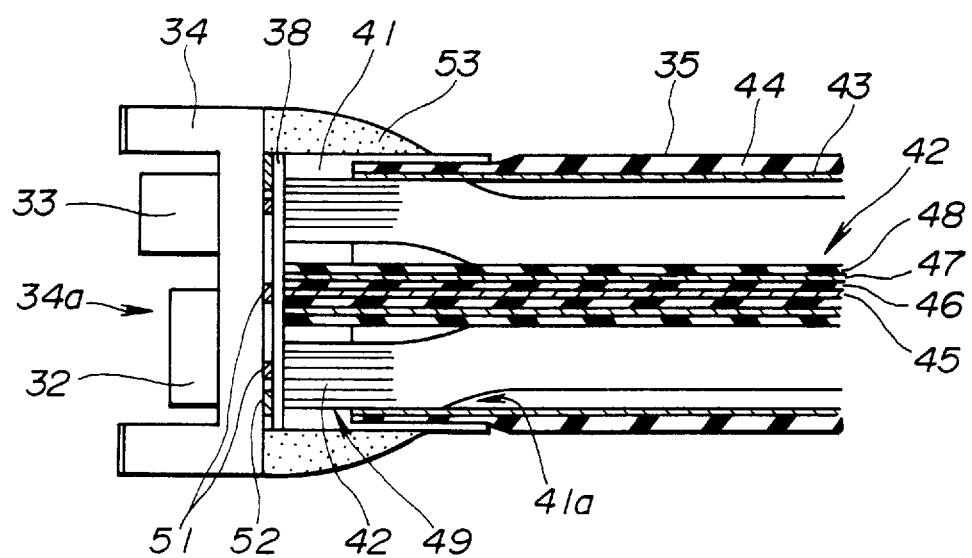

As shown in FIG. 6, for connecting the seven-core composite cable 35 to the HIC board 34, first, the HIC board 34 and seven-core composite cable 35 are opposed to each other and aligned with each other. Next, the anisotropic conducting sheet 38 is placed on the distal side of the seven-core composite cable 35. The distal side of the insulating block 41 attached to the distal side of the seven-core composite cable 35 is then press-fitted on the plane of the HIC board 34. The signal electrodes 51 on the HIC board 34 and the inner conductors 45 of the coaxial cables 42 of the seven-core composite cable 35, and the ground electrodes 52 on the HIC board 34 and the outer conductors 47 of the coaxial cables 42 of the seven-core composite cable 35 are mutually electrically connected all at once. The perimeter of the joint is secured by applying, for example, an epoxy adhesive 53 for the purpose of reinforcement.

Incidentally, the anisotropic conducting sheet 38 can be press-fitted in pitches of up to 50 um. The conditions for press-fitting may be such that the temperature ranges from 165° to 180° C., the pressure ranges from 10 to 20 kg/cm$^2$, and the time ranges from 20 to 30 sec.

As mentioned above, an insulating block that retains the aligned form of coaxial cables contained in a composite cable and that accommodates the coaxial cables is unitedly attached to the distal part of the composite cable. Moreover, an HIC board has electrodes opposed to conductors placed in the insulating block attached to the distal part of the composite cable. The distal side of the insulating block can thus be opposed to the plane of the HIC board, and then press-fitted thereto with the anisotropic conducting sheet interposed between the distal side of the insulating block and the plane of the HIC board. This makes it possible to electrically connect the conductors of the composite cable to the electrodes on the HIC board all at once. Consequently, the HIC board and composite cable can be readily connected to each other without the necessity of the work of routing cables. This results in improved workability. Moreover, the reliability of the joint between the HIC board and composite cable improves greatly.

Moreover, since press-fitting is carried out with the anisotropic conducting sheet placed, a rigid area is not newly formed between each of the conductors of the composite cable and each of the electrodes on the HIC board. Consequently, the length of a rigid section can be reduced greatly.

FIGS. 7 to 11 show the second embodiment of the present invention.

To begin with, the structure of a composite cable will be described.

Figure 7:
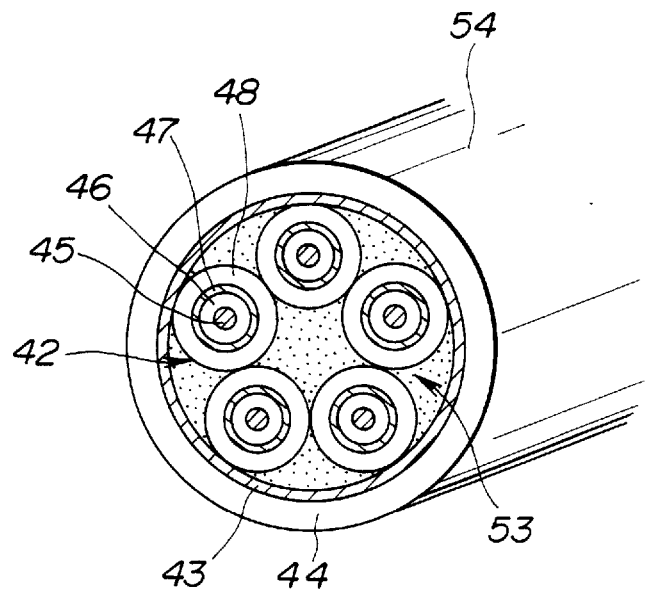
FIGS. 7 to 11 relate to the second embodiment of the present invention.

As shown in FIG. 7, a composite cable in this embodiment is a five-core composite cable 54 made by bundling up five coaxial cables 42. The outer circumferences of the five coaxial cables 42 are covered by a synthetic shield 43. The synthetic shield 43 is coated with a synthetic coat 44.

The spaces among the coaxial cables 42 of the five-core composite cable 54 are filled with an adhesive 53, whereby a hardened portion of approximately 2 mm long from the distal side is formed. The hardened portion hardened by the adhesive 53 is cut out at a position of approximately 1 mm from the distal side. This results in the illustrated five-core composite cable 54. As illustrated, the distal side is formed as a plane, and the five coaxial cables 42 are exposed concentrically on the plane.

Figure 8:
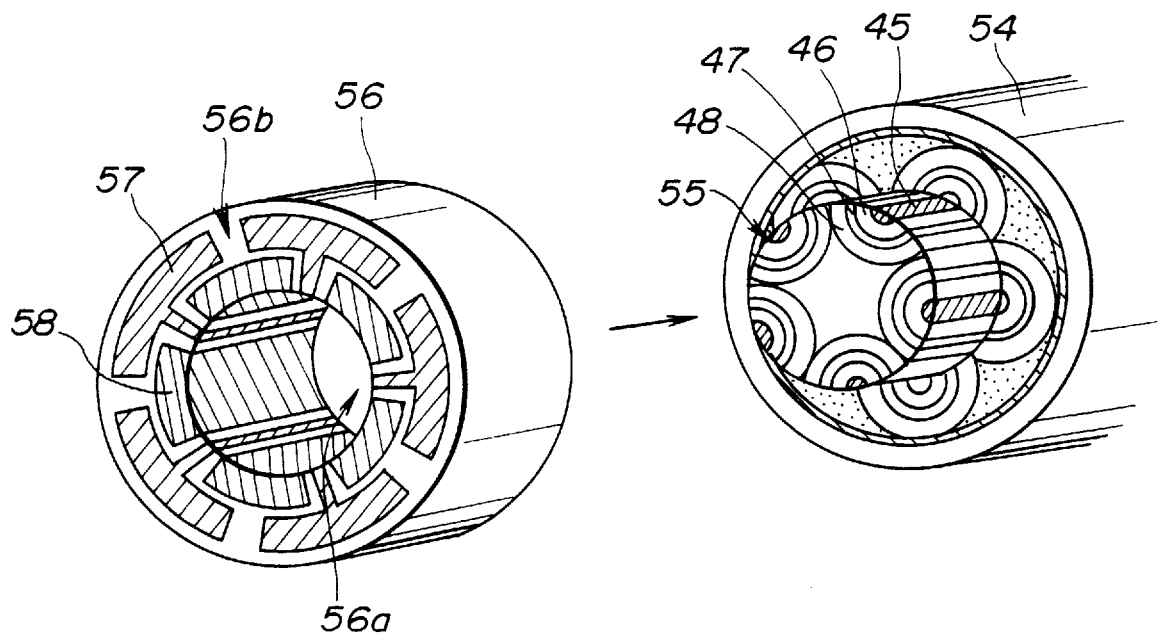

As shown in FIG. 8, the perimeter of the five-core composite cable 54 of 1 mm long from the distal side of the five-core composite cable 54 that is hardened by the adhesive 53 is cut out so that the centers of the inner conductors 45 of the coaxial cables 42 are left intact. Thus, the distal part of the five-core composite cable 54 has a desired shape. Consequently, a cylindrical convex part 55 of approximately 1 mm long is formed on the distal side of the five-core composite cable 54.

Next, a tubular member serving as an aligning means to be fitted on the cylindrical convex part 55 formed on the distal side of the five-core composite cable 54 will be described.

As shown in FIG. 8, a tubular member 56 into which the cylindrical convex part 55 formed on the distal side of the five-core composite cable 54 is fitted is a round tube having a through hole 56a formed so that its inner diameter becomes substantially identical to the outer diameter of the cylindrical convex part 55. Conducting patterns that will be described later are formed on the inner circumferential side of the through hole 56a of the tubular member 56 and on the distal side 56b.

The conducting patterns formed on the tubular member 56 include signal conducting patterns 57 formed so that when the through hole 56a of the tubular member 56 is fitted on the cylindrical convex part 55, the signal conducting patterns 57 can be connected to the inner conductors 45 of the coaxial cables 42 of the five-core composite cable 54, and ground conducting patterns 58 formed to be connected to the outer conductors 47 of the coaxial cables 42.

The ground conducting patterns 58 each have a large width on the inner circumferential side so that the outer conductors 47 of the adjoining coaxial cables 42 can be connected mutually. On the distal side 56b of the tubular member 56, the ground conducting patterns 58 are exposed widely along the inner circumferential boundary, and the signal conducting patterns 57 are exposed widely along the outer circumferential boundary.

Figure 9:
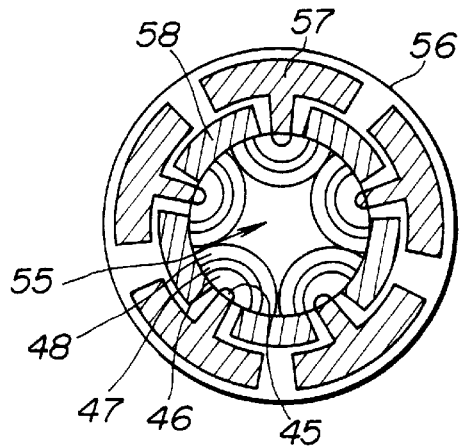

As shown in FIG. 9, when the tubular member 56 is fitted on the cylindrical convex part 55 of the five-core composite cable 54, the signal conducting patterns 57 that are conducting patterns on the tubular member 56 and the inner conductors 45, and the ground conducting patterns 58 and outer conductors 47 are connected mutually. At this time, the distal side of the five-core composite cable 54 will not jut out from the distal side of the tubular member 56.

Next, an HIC board to which the conducting patterns of the five-core composite cable 54 with the tubular member 56 fitted thereon will be described.

Figure 10:
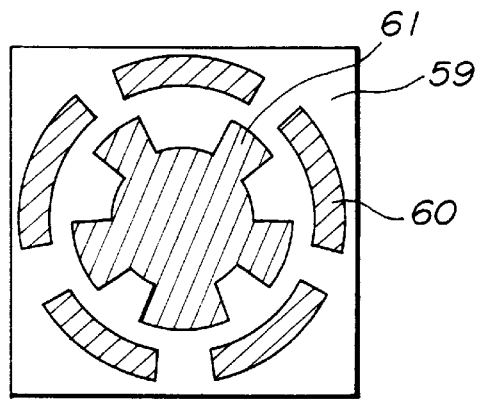

As shown in FIG. 10, the electrodes on an HIC board 59 are formed by the number of the coaxial cables 42 so that the electrodes will coincide with the conducting patterns formed on the tubular member 56; that is, all the ground conducting patterns 58 will be connected to ground conductors 61 and the signal conducting patterns 57 will be connected to signal conductors 60.

The other components are identical to those in the first embodiment. The same members will be assigned the same reference numerals. The description of the members will be omitted.

The connection of the five-core composite cable 54 with the tubular member 56 attached to the distal part thereof as mentioned above and the HIC board 59 will be described.

Figure 11:
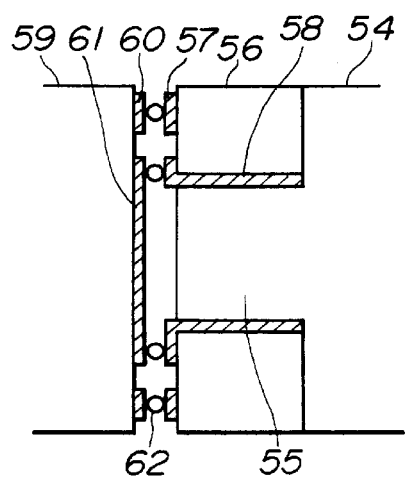

As shown in FIG. 11, the five-core composite cable 54 is opposed to the HIC board 59 and aligned therewith, whereby the conducting patterns 57 and 58 are opposed to the electrodes 60 and 61. The electrodes 60 and 61 on the HIC board 59 are electrically connected to the conducting patterns 57 and 58 on the tubular member 55 attached to the distal part of the five-core composite cable 54 via bumps 62. After the conducting patterns 57 and 58 are connected to the electrodes 60 and 61, similarly to the first embodiment, the perimeter of the joint is fixed using the adhesive 53 or the like for the purpose of reinforcement.

As mentioned above, the distal part of a composite cable is filled with an adhesive and hardened, and then machined to have a desired shape. Moreover, a tubular member having conducting patterns is attached to the machined distal part. Consequently, the joint between conductors of coaxial cables contained in the composite cable and conducting patterns on the tubular member, and the joint between the conducting patterns on the tubular member attached to the composite cable and conductors formed on an HIC board can be made large. This results not only in greatly-improved workability but also in greatly-improved reliability.

Moreover, since setting is made so that the distal side of a five-core composite cable lies backward relative to the distal side of the tubular member, there is no concern about the incident that the conductors on the distal side of a cylindrical convex part come into contact with the ground conductors formed on the HIC board. When the distal side of the cylindrical convex part is machined, it is unnecessary to especially finely cut or polish the distal end. This results in a reduced man-hour for machining and a reduced price.

The other operations and advantages are identical to those of the first embodiment.

FIGS. 12 to 17 show the third embodiment of the present invention.

To begin with, the structure of a composite cable will be described.

Figure 12:
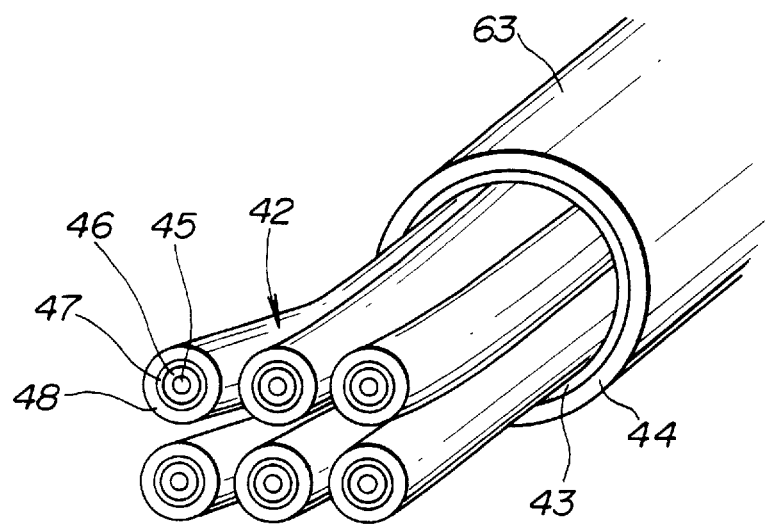
FIGS. 12 to 17 relate to the third embodiment of the present invention.

As shown in FIG. 12, a composite cable in this embodiment is a six-core composite cable 63 made by bundling up six coaxial cables 42. The outer circumference of the six bundled coaxial cables 42 is covered by a synthetic shield 43. The outer circumference of the synthetic shield 43 is coated with a synthetic coat 44.

In the distal part of the six-core composite cable 63, the synthetic coat 44 and synthetic shield 43 are stripped off in the range of several millimeters from the distal side. The six coaxial cables are therefore separated from one another.

Figure 13:
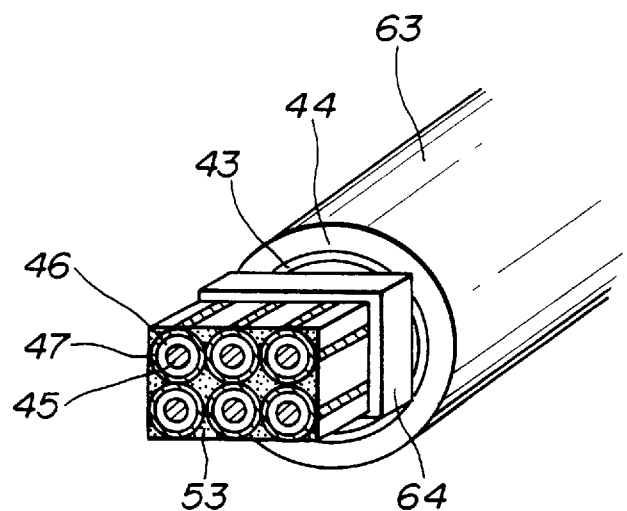

As shown in FIG. 13, after outer insulators 48 of the six separated coaxial cables 42 are stripped off in the range of several millimeters, the six coaxial cables 42 are arranged in a desired form, for example, up and down in two rows in threes, and then fixed using an adhesive 53 so that the sectional shape will be rectangular.

After the six coaxial cables 42 of the six-core composite cable 63 are arranged in two rows in threes and then hardened so that the sectional shape will be rectangular, a rectangular metallic frame 64 is fitted on the outer circumference of the hardened distal part. At this time, the metallic frame 64 is pushed until it abuts against the stripped side of the six-core composite cable 63 and then secured. The outer conductors 47 of all the coaxial cables 42 of the six-core composite cable 63 and the synthetic shield 43 conduct via the metallic frame 64.

For hardening the six coaxial cables 42 by applying the adhesive 53 so that the sectional shape of the bundled coaxial cables will be rectangular, it is recommended that the six coaxial cables 42 be encased in dies and then hardened by applying the adhesive.

Figure 14:
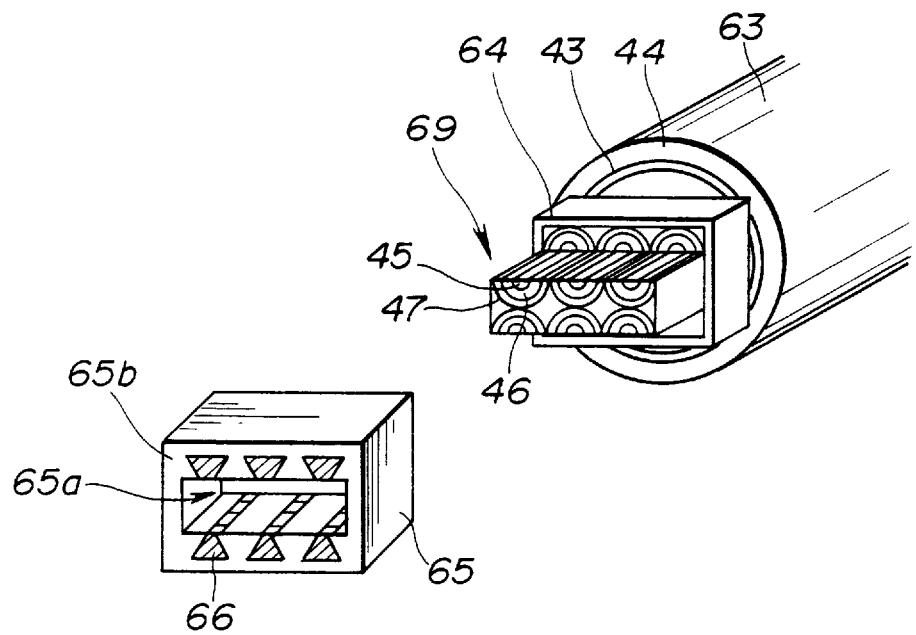

As shown in FIG. 14, the three upper coaxial cables 42 and three lower coaxial cables 42 are cut from the ends thereof substantially along the center lines of the inner conductors 45 arranged up and down in two rows. Thus, a parallelepiped convex part 69 is formed on the front side of the metallic frame 64.

Next, a tubular member serving as an aligning means to be fitted on the parallelepiped convex part 69 formed on the distal side of the six-core composite cable 64 will be described.

As shown in FIG. 14, a resin frame 65 to be fitted on the parallelepiped convex part 69 formed on the distal side of the six-core composite cable 63 is a square tube having a square hole 65a that is shaped substantially like the contour of the parallelepiped convex part 69.

The inner circumferential side of the square hole 65a of the resin frame 65 and the distal side 65b have signal conducting patterns 66 to be connected to the inner conductors 45 of the six-core composite cable 63. The length of the resin frame 65 is slightly larger than the length of the parallelepiped convex part 69. The resin frame 65 is formed with an insulating resin member. Alternatively, the frame 65 may be made of an insulating ceramic.

Figure 15:
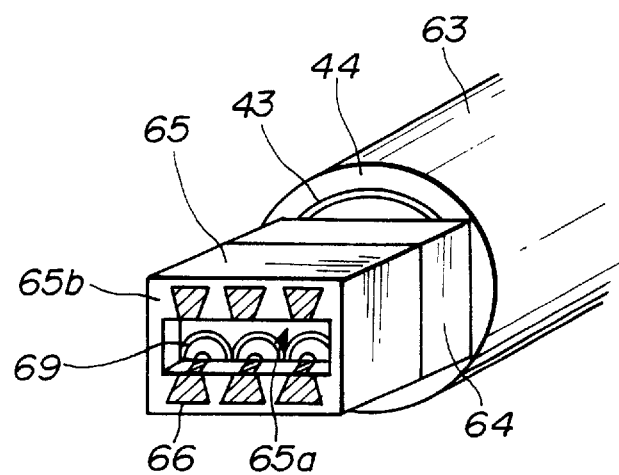

As shown in FIG. 15, when the resin frame 65 is fitted on the parallelepiped convex part 69 formed on the distal side of the six-core composite cable 63, all the inner conductors 45 of the coaxial cables 42 of the six-core composite cable 63 are connected to the signal conducting patterns 66 on the inner circumferential side of the square hole 65a of the resin frame 65, and led to the signal conducting patterns 66 exposed on the distal side 65b. By contrast, the outer conductors 47 and synthetic shield 43 of the six-core composite cable 63 all conduct via the metallic frame 64.

The metallic frame 64 works as a ground. The continuity of the shield frame 39 with the metallic frame 64 should therefore be attained using a conductive adhesive or conductive resin. The adhesive 53 may be of an insulating type. In this case, after the outer conductors 47 are bared, the metallic frame 64 is attached. Furthermore, the outer insulators 48 may be made of a material different from the inner insulators 46, so that the outer insulators 48 alone can be melted using a chemical. This obviates the necessity of stripping off the outer insulators 48.

Next, an HIC board to which the conducting patterns of the six-core composite cable 63 with the resin frame 65 fitted thereon will be described.

Figure 16:
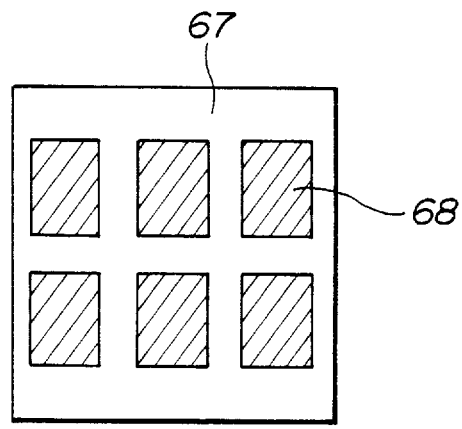

As shown in FIG. 16, signal conductors 68 are formed on an HIC board 67 coincidentally with the six coaxial cables 42 so that the signal conductors 68 are opposed to the signal conducting patterns 66 exposed on the distal side 65a of the resin frame 65.

The connection of the six-core composite cable 63 with the resin frame 65 fitted on the distal part thereof having the aforesaid structure and the HIC board 67 will be described.

Figure 17:
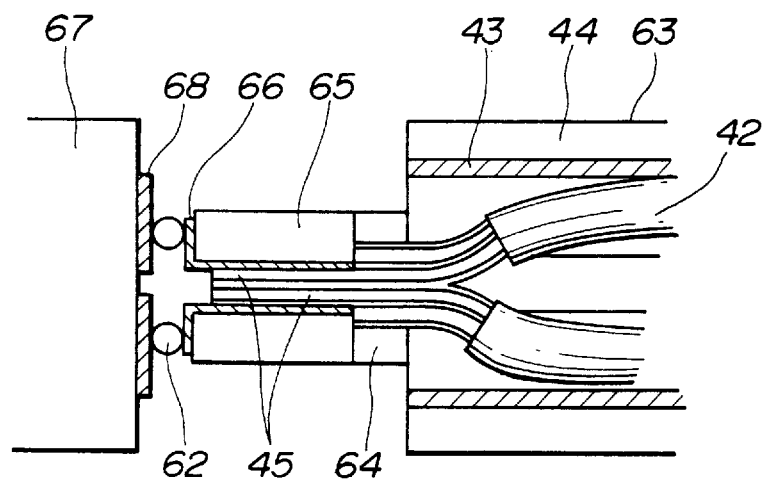

As shown in FIG. 17, the HIC board 67 is opposed to the six-core composite cable 63 and aligned therewith, whereby the conducting patterns 66 are opposed to the electrodes 68. The electrodes 68 on the HIC board 67 are electrically connected to the conducting patterns 66 of the resin frame 65 fitted on the distal part of the six-core composite cable 63 via bumps 62. After the conducting patterns 66 and electrodes 68 are mutually connected, similarly to the first embodiment, the perimeter of the joint is fixed using an adhesive 53 or the like for the purpose of reinforcement.

As mentioned above, a synthetic shield and synthetic coat are stripped off in the range of several millimeters from the distal side of a composite cable. Mutually-separated coaxial cables are hardened in a desired form by applying an adhesive. The distal part of the hardened coaxial cables is machined in a desired shape. A resin frame having conducting patterns is attached to the machined distal part. The joint between the conductors of coaxial cables contained in the composite cable and the conducting patterns on the resin frame, and the joint between the conducting patterns on the resin frame attached to the composite cable and the conductors on the HIC board can be formed to be of one kind. This simplifies the arrangements of the conducting patterns on the resin frame and of the electrodes on the HIC board. Consequently, the man-hour required for machining and that required for assembling are reduced. This results in improved workability and improved reliability of connections.

The connection between the conducting patterns and electrodes is, similarly to the second embodiment, achieved via bumps. Alternatively, similarly to the first embodiment, an anisotropic conducting sheet may be used for the connection. Moreover, the signal conducting patterns may be led to the outer circumferential side of the parallelepiped convex part, and then connected and fixed to the electrodes by performing soldering.

Figure 18:
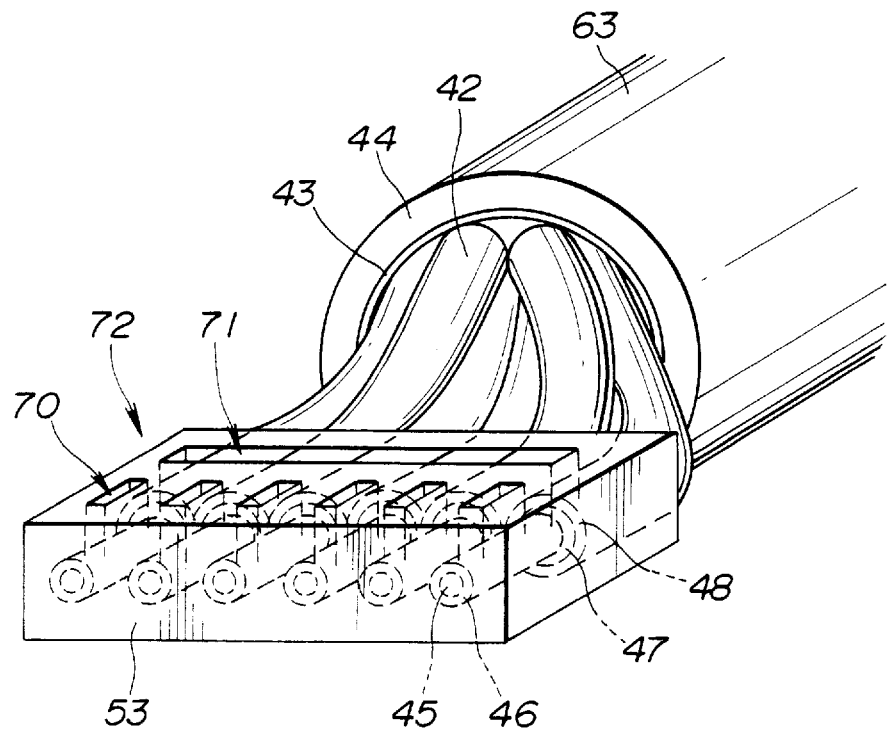
FIGS. 18 to 20 relate to a variant of the third embodiment.
Figure 19:
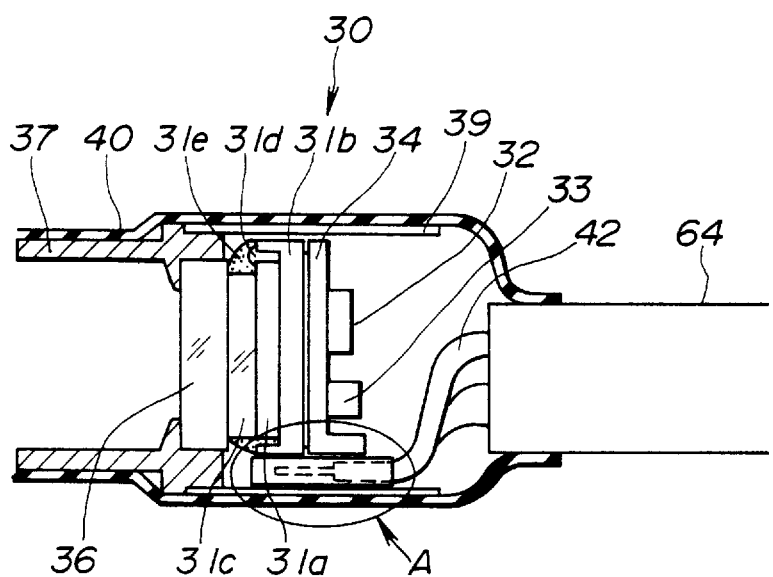
Figure 20:
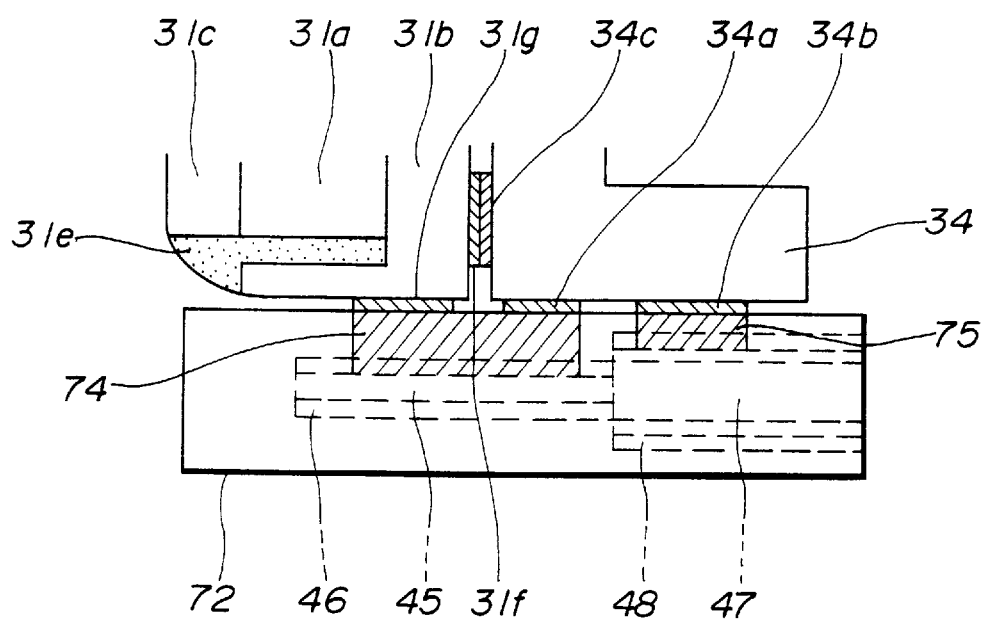

FIGS. 18 to 20 show a variant of the third embodiment.

As shown in FIG. 18, the six-core composite cable 63 in this embodiment has the synthetic shield 43 and synthetic coat 44 stripped off in the range of several millimeters from the distal side of the cable. The six coaxial cables 42 are therefore separated from one another. After these six coaxial cables 42 have the outer insulators 48 and outer conductors 47 of the distal parts thereof stripped off by the same length. The stripped distal parts are aligned with one another. The coaxial cables 42 are then arranged sideways in a row and fixed by means of the adhesive 53 used as an aligning means so that the coaxial cables 42 will substantially form a parallelepiped. Thus, a distal joint 72 is formed. In other words, the distal joint 72 is shaped like a plate whose thickness is slightly larger than the outer diameter of each of the coaxial cables 42.

Signal ditches 70 and a ground ditch 71 are machined at positions coincident with the inner conductors 45 and outer conductors 47 arranged inside the plate-like distal joint 72. The signal ditches 70 and ground ditch 71 are formed by laser machining; that is, formed by irradiating a laser beam toward given positions. Specifically, when a laser beam is irradiated to the adhesive hardened in the form of a plate, the output is adjusted properly in order to machine only the adhesive 53 and inner insulators 46 or only the adhesive 53 and outer insulators 48. Thus, machining is carried out so that a laser beam will not reach the inner conductors 45 and outer conductors 47.

The signal ditches 70 are formed to coincide with the inner conductors 45, while the ground ditch 71 is continuous over the outer conductors 47 arranged sideways in a row. The ditch spaces of the signal ditches 70 and ground ditch 71 are filled with a conductive adhesive, whereby conducting patterns 74 and 75 are formed.

The connection of the distal joint 72 will be described.

As shown in FIGS. 19 and 20, the electrodes 31f of the CCD 31 are formed on the back side of the ceramic package 31b, and the signal electrodes 31a are formed on the lateral side thereof. On the other hand, the electrodes 34c are formed on the proximal-side plane of the HIC board 34 on which the chip capacitor 33 and IC 32 are not mounted, and the signal electrodes 34a and ground electrodes 34b are formed on the lateral side thereof.

Among the electrodes arranged on the lateral side of the HIC board 34, the signal electrodes 34a used to transfer signals and the ground electrodes 34b used for grounding are arranged mutually separately on the distal side and proximal side respectively. The distal joint 72 formed on the distal part of the six-core composite cable 63 is connected to the lateral side of a unit made by connecting the CCD 31 and HIC board 34. At this time, the signal ditches 70 of the distal joint 72 are connected to the signal electrodes 31g on the CCD chip 31, and the ground ditch 71 of the distal joint 72 is connected to the signal conducting patterns 34b.

As mentioned above, conducting patterns on a distal joint formed on a composite cable is connected to electrodes that are formed on the lateral side of a unit made by connecting a CCD and HIC board. The connection of the composite cable and HIC board can be achieved without the necessity of increasing the length of a rigid section.

The other operations and advantages are identical to those of the aforesaid embodiments.

The relationships between the aforesaid embodiments and the numbers of cores of a composite cable are not limited to the aforesaid ones. Any number of cores of a composite cable and any embodiment can be combined freely. The number of cores contained in a composite cable and the kind of cables contained therein are not limited to the aforesaid numbers of cores and coaxial cable respectively.

According to the aforesaid embodiments, the work of connecting cables contained in a composite cable to electrodes on a printed-circuit board can be achieved easily, and the length of a rigid section can be reduced.

In the present invention, it will be apparent that a wide range of different embodiments can be formed on the basis of the present invention without a departure from the spirit and scope of the invention. This invention will be limited to the appended claims but not restricted to any specific embodiments.

What is claimed is:

1. An imaging apparatus, comprising:
   a solid-state imaging device;
   a printed-circuit board connected to said solid-state imaging device, said printed-circuit board having a plane part with electrodes;
   a composite cable having a bundled plurality of cables, with ends of the bundled plurality of cables on a distal side of said composite cable facing the plane part of the printed-circuit board being a distal part; and
   aligning means having at least one hole into which the bundled plurality of cables is inserted in a desired aligned form for electrical connection with the electrodes on the plane part of said printed-circuit board.

2. An imaging apparatus according to claim 1, wherein said distal part of said composite cable corresponds with the shape of the hole of said aligning means.

3. An imaging apparatus according to claim 2, wherein the desired aligned form of said bundled plurality of cables corresponds to an original arrangement of the bundled plurality of cables in said composite cable.

4. An imaging apparatus according to claim 3, wherein said aligning means is a tubular member and the hole of said aligning means includes a plurality of through holes, into which each of the bundled plurality of cables are respectively inserted.

5. An imaging apparatus according to claim 4, further comprising an anisotropic conducting member interposed between said tubular member and said electrodes on said printed-circuit board.

6. An imaging apparatus according to claim 1, wherein said distal part of said composite cable includes an adhesive securing the bundled plurality of cables in a desired arrangement.

7. An imaging apparatus according to claim 6,
   wherein the adhesive and the bundled plurality of cables in the distal part form a convex part which is cylindrical and concentric with a contour of said composite cable; and
   wherein each of the bundled plurality of cables has a conductor which is exposed along an outer circumferential side of said convex part.

8. An imaging apparatus according to claim 7, wherein said aligning means is a tubular member and said convex part is fitted into the hole of said tubular member;
   wherein said tubular member has an inner circumferential side defining the hole and conducting patterns on the inner circumferential side corresponding to the conductors exposed on the outer circumferential side of said convex part; and
   wherein said conducting patterns are exposed on a distal side of said tubular member facing said plane part of said printed-circuit board.

9. An imaging apparatus according to claim 8, wherein said conducting patterns exposed on the distal side of said tubular member are electrically connected by bumps to the electrodes on the plane part of said printed-circuit board.

10. An imaging apparatus according to claim 6,
wherein the adhesive secures the bundled plurality of cables in two rows in the desired arrangement to form a rectangular convex part; and
wherein each of the bundled plurality of cables has a conductor which is exposed on outer opposing sides of the rectangular convex part.

11. An imaging apparatus according to claim 10, wherein said aligning means is a frame and the hole is a rectangular hole that is fitted on said rectangular convex part, the frame having conductor patterns extending from the hole onto a distal side of the frame facing the plane part of said printed-circuit board, the conductor patterns corresponding to the exposed conductors of the bundled plurality of cables.

12. An imaging apparatus according to claim 6,
wherein the adhesive secures the bundled plurality of cables in a row in the desired arrangement; and
wherein said aligning means is a plate-like frame having the hole into which the row of the bundled plurality of cables is inserted.

13. An imaging apparatus according to claim 12,
wherein the plate-like frame has ditches opened over a lengthwise side of each of the bundled plurality of cables and filled with a conductive material; and
wherein each of the bundled plurality of cables has a conductor exposed to and contacting with the conductive material in the ditches of the plate-like frame.

14. An imaging apparatus, comprising:
a solid-state imaging device;
a printed-circuit board connected to said solid-state imaging device, said printed-circuit board having a plane part with electrodes;
a composite cable having a bundled plurality of cables in an original arrangement; and
a tubular member having a plurality of through holes into which each of the bundled plurality of cables is respectively inserted in the original arrangement for electrical connection with the electrodes on the plane part of said printed-circuit board.

15. An imaging apparatus, comprising:
a solid-state imaging device;
a printed-circuit board connected to said solid-state imaging device, said printed-circuit board having a plane part with electrodes;
a composite cable having a bundled plurality of cables secured in a circular arrangement with an adhesive and having a cylindrical distal part located at a distal end of said composite cable to be connected to the electrodes of said printed-circuit board, each of the bundled plurality of cables has an inner conductor exposed on an outer circumferential side of the distal part; and
a tubular member having a through hole into which the distal part is inserted and having conducting patterns extending from within the through hole onto a distal side of the tubular member facing the plane part of said printed-circuit board, each of the conducting patterns within the through hole are respectively electrically connected to each of the exposed conductors of the bundled plurality of cables of the distal part, the conducting patterns on the distal side of the tubular member are electrically connected with the electrodes on the plane part of said printed-circuit board.

16. An imaging apparatus according to claim 15,
wherein each of the bundled plurality of cables further includes an outer grounding layer which is also exposed on the circumferential side of the distal part; and
wherein the conducting patterns of said tubular member includes signal conducting patterns electrically connected to the exposed inner conductors within the through hole and ground conducting patterns electrically connected to the exposed ground layers within the through hole, the ground conducting patterns extending onto an inner periphery of the distal side of said tubular member adjacent to the through hole, and the signal conducting patterns extending outwards along an outer periphery of the distal side of said tubular member beyond the ground conducting patterns.

17. An imaging apparatus according to claim 16, wherein the electrodes on the plane part of said printed-circuit board include a central ground electrode electrically connected to the ground conducting patterns and a plurality of signal electrodes surrounding the central ground electrode, each of the signal electrodes respectively electrically connected to each of the signal conducting patterns on the distal side of said tubular member.

18. An imaging apparatus, comprising:
a solid-state imaging device;
a printed-circuit board connected to said solid-state imaging device, said printed-circuit board having a plane part with electrodes;
a composite cable having a bundled plurality of cables secured in a rectangular arrangement with an adhesive at a rectangular distal part located at a distal end of said composite cable to be connected to the electrodes of said printed-circuit board, each of the bundled plurality of cables has an inner conductor exposed on opposing sides of the distal part; and
a frame having a rectangular through hole into which the rectangular distal part is inserted and having conducting patterns extending from within the through hole onto a distal side of said frame facing the plane part of said printed-circuit board, each of the conducting patterns within the through hole are respectively electrically connected to each of the exposed conductors of the bundled plurality of cables of the distal part, the conducting patterns on the distal side of said frame are electrically connected with the electrodes on the plane part of said printed-circuit board.

19. An imaging apparatus, comprising:
a solid-state imaging device;
a printed-circuit board connected to said solid-state imaging device, said printed-circuit board having a plane part and a lateral plane part with electrodes;
a composite cable having a bundled plurality of cables secured in a single row arrangement with an adhesive at a rectangular distal part located at a distal end of said composite cable opposing the plane part of said printed-circuit board, each of the bundled plurality of cables has an inner conductor exposed on opposing sides of the distal part; and
a plate-like frame having a rectangular hole extending along a flatness of said plate-like frame into which the rectangular distal part is inserted and having ditches opened on one side of said plate-like frame over the exposed inner conductors of the bundled plurality of cables at the distal part, the ditches are filled with a conductive material contacting the exposed inner conductors of the bundled plurality of cables, the conductive material at a surface of the ditches are electrically connected with the electrodes on the lateral plane part of said printed-circuit board.

* * * * *